United States Patent
Shimamori et al.

(10) Patent No.: US 9,970,948 B2
(45) Date of Patent: May 15, 2018

(54) AUTOMATIC ANALYZER

(71) Applicant: HITACHI HIGH-TECHNOLOGIES CORPORATION, Tokyo (JP)

(72) Inventors: Toshiyuki Shimamori, Tokyo (JP); Akihisa Makino, Tokyo (JP); Masato Ishizawa, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days. days.

(21) Appl. No.: 15/025,586

(22) PCT Filed: Oct. 22, 2014

(86) PCT No.: PCT/JP2014/078008
§ 371 (c)(1),
(2) Date: Mar. 29, 2016

(87) PCT Pub. No.: WO2015/079829
PCT Pub. Date: Jun. 4, 2015

(65) Prior Publication Data
US 2016/0238620 A1 Aug. 18, 2016

(30) Foreign Application Priority Data

Nov. 26, 2013 (JP) ................................. 2013-243452

(51) Int. Cl.
*G01N 33/86* (2006.01)
*G01N 35/10* (2006.01)
(Continued)

(52) U.S. Cl.
CPC ........... *G01N 33/86* (2013.01); *G01N 33/491* (2013.01); *G01N 35/1002* (2013.01);
(Continued)

(58) Field of Classification Search
None
See application file for complete search history.

(56) References Cited

U.S. PATENT DOCUMENTS

| 4,252,536 A | 2/1981 | Kishimoto |
| 5,555,767 A | 9/1996 | Makino et al. |

(Continued)

FOREIGN PATENT DOCUMENTS

| EP | 0 607 442 A1 | 7/1994 |
| EP | 1 890 142 A2 | 2/2008 |

(Continued)

OTHER PUBLICATIONS

Artel, Dispensing a Sample from a Pipette into a Target Receptacle, Oct. 23, 2013 accessed at www.artel-usa.com/dispensing-a-sample-from-a-pipette-into-a-target-receptacle/ on Oct. 11, 2017, 1-3 pages.*

(Continued)

*Primary Examiner* — P. Kathryn Wright
(74) *Attorney, Agent, or Firm* — Mattingly & Malur, PC (57) ABSTRACT

If an air bubble is entrained when a reagent is added to a sample, disturbance caused by this air bubble may prevent accurate optical measurement, thereby reducing accuracy for measuring blood clotting ability. The position to dispense the reagent depends on accuracy of stopping a reagent dispensing mechanism and dimensional errors of individual detectors, and thus conventional reagent discharging method may entrain an air bubble because a distance between a nozzle for dispensing the reagent and an inner wall of a reaction vessel is not constant and conditions for dispensing the reagent to the sample vary. In the present invention, an automatic analyzer with a nozzle for sucking and discharging the reagent for blood clotting reaction is provided with a dispensing mechanism that keeps a constant position for the nozzle to discharge the reagent by pressing the nozzle (Continued)

against the inner wall of the reaction vessel within the elastic range.

11 Claims, 5 Drawing Sheets

(51) Int. Cl.
  *G01N 33/49* (2006.01)
  *G01N 35/04* (2006.01)
  *G01N 35/00* (2006.01)
(52) U.S. Cl.
  CPC ..... *G01N 35/1011* (2013.01); *G01N 35/1016* (2013.01); *G01N 35/1083* (2013.01); *G01N 2035/00346* (2013.01); *G01N 2035/0453* (2013.01); *G01N 2035/1058* (2013.01); *G01N 2800/224* (2013.01)

(56) References Cited

U.S. PATENT DOCUMENTS

| 2008/0044311 A1 | 2/2008 | Iguchi et al. |
| 2008/0044912 A1 | 2/2008 | Yamamoto et al. |
| 2012/0315190 A1* | 12/2012 | Adachi ............ G01N 21/51 422/82.05 |
| 2014/0199779 A1 | 7/2014 | Yasui et al. |

FOREIGN PATENT DOCUMENTS

| JP | 59028642 A | * | 2/1984 |
| JP | 07-239334 A | | 9/1995 |
| JP | 2003-035715 A | | 2/2003 |
| JP | 2003-057249 A | | 2/2003 |
| JP | 2005-257491 A | | 9/2005 |
| JP | 2008-046031 A | | 2/2008 |
| JP | 2008-070355 A | | 3/2008 |
| JP | 2010117222 A | * | 5/2010 |
| JP | 2010-271203 A | | 12/2010 |
| WO | 2013/042404 A1 | | 3/2013 |

OTHER PUBLICATIONS

International Search Report of PCT/JP2014/078008 dated Nov. 25, 2014.
Extended European Search Report received in corresponding European Application No. 14865780.2 dated Jun. 30, 2017.

* cited by examiner

MOTION OF NOZZLE WHEN
DISPENSING REAGENT

[FIG. 7]

ROTATION DIRECTION OF LIQUID
WHEN DISCHARGING LIQUID

AUTOMATIC ANALYZER

TECHNICAL FIELD

The present invention relates to an automatic analyzer that analyzes the amount of a component contained in a sample such as blood or urine.

BACKGROUND ART

As an analyzer that analyzes the amount of a component contained in a sample (hereinafter also referred to as "specimen"), there has been known an automatic analyzer that measures the amount of transmitted light or the amount of scattered light with a single wavelength or a plurality of wavelengths obtained by irradiating light from a light source onto a reaction mixture obtained by mixing a sample with a reagent, and calculates the amount of the component based on the relationship between the amount of light and the concentration. In the reaction of the reaction mixture, there are roughly two types of analysis fields as follows: a colorimetric analysis using a coloring reaction between a substrate and an enzyme; and a homogeneous immunoassay using an agglutination reaction by binding of an antigen to an antibody. As the latter homogeneous immunoassay, there have been known measurement methods such as an immunonephelometric method and a latex agglutination method.

In an immunonephelometric method, a reagent containing an antibody is used, and an immune complex of the reagent with a measurement target (antigen) contained in a sample is formed, the resulting immune complex is optically detected, and the amount of a component is quantitatively determined. In a latex agglutination method, a reagent containing latex particles sensitized (bound) with an antibody on the surfaces thereof is used and the latex particles are agglutinated by an antigen-antibody reaction with an antigen contained in a sample, the resulting agglutinated particles are optically detected, and the amount of a component is quantitatively determined. Further, there has also been known a heterogeneous immunoassay device that performs an immunoassay with higher sensitivity by employing a detection technique using chemiluminescence or electrochemical luminescence and a B/F separation technique.

In addition, there has also been an automatic analyzer that measures a blood clotting ability. Blood maintains its fluidity in blood vessels and flows therethrough. However, once bleeding occurs, a clotting factor present in plasma or platelets is activated in a chain reaction, and fibrinogen in plasma is converted to fibrin, and the fibrin is deposited, whereby bleeding is arrested. Such a blood clotting ability includes an extrinsic one in which blood leaking outside the blood vessel clots and an intrinsic one in which blood clots in the blood vessel. The measurement items with respect to the blood clotting ability (blood clotting time) include a prothrombin time (PT) in an extrinsic blood clotting reaction test, an activated partial thromboplastin time (APTT) and a fibrinogen level (Fbg) in an intrinsic blood clotting reaction test, and the like.

For all these items, it is necessary to sufficiently stir a mixed liquid of a sample and a reagent for allowing a blood clotting reaction to stably proceed. Therefore, in PTL 1, as a general stirring method in an automatic analyzer, a method of performing stirring by immersing a stirring bar in a material to be stirred is described. In addition, in PTL 2, non-contact stirring is realized by stirring a sample and a reagent with ultrasound, and therefore, a risk of carrying a component of a material to be stirred in a material to be stirred subsequently is eliminated. Further, if an air bubble is entrained in a mixed liquid when a reagent is added to a sample, disturbance caused by this air bubble may hinder accurate optical measurement, thereby reducing accuracy of measuring a blood clotting ability. Therefore, PTL 3 discloses as a method of preventing air bubble entrainment in a mixed liquid when a reagent is dispensed into a sample, a technique for dropping a reagent along the inner wall of a reaction vessel when the reagent is dispensed by using a dispensing mechanism in which the tip of a nozzle has a substantially circular arc shape when the reagent is dispensed into the sample.

CITATION LIST

Patent Literature

PTL 1: JP-A-2003-57249
PTL 2: JP-A-2003-035715
PTL 3: JP-A-2008-070355

SUMMARY OF INVENTION

Technical Problem

It is necessary to sufficiently stir a mixed liquid of a sample and a reagent for allowing a blood clotting reaction to stably proceed.

In PTL 1, a method of performing stirring by immersing a stirring bar in a material to be stirred is described. However, in a blood clotting reaction, a clotting reaction starts immediately after dispensing a reagent into a sample, and therefore, when stirring is performed using a stirring bar, a clotted material of blood is easily adhered to the stirring bar. Due to this, when a material to be stirred subsequently is stirred, a risk of carrying a component of a material stirred previously therein is increased, and therefore, an accurate analysis may not be able to be performed. In PTL 2, non-contact stirring is realized by stirring a sample and a reagent with ultrasound, and therefore, a risk of carrying a component of a material to be stirred in a material to be stirred subsequently is eliminated. However, a clotting reaction starts from the moment when a reagent is added to a sample, and the reaction is completed in about 10 seconds at the earliest. In a colorimetric analysis or a homogeneous immunoassay, the reaction lasts for a few minutes, and an analysis result can be obtained by measuring the reaction process at a few points. However, in a clotting reaction, in general, a favorable measurement result cannot be obtained unless the reaction process is measured at all times from the initiation of the reaction to the completion of the reaction. Due to this, when stirring is performed for several seconds with a stirring mechanism or the like after a reagent is added to a sample, an accurate reaction process cannot be measured, and therefore, a favorable measurement result cannot be obtained. In addition, if an air bubble is entrained in a mixed liquid when a reagent is added to a sample, disturbance caused by this air bubble may hinder accurate optical measurement, thereby reducing accuracy of measuring a blood clotting ability.

On the other hand, in PTL 3, as a method of preventing air bubble entrainment in a mixed liquid when a reagent is dispensed into a sample, a reagent is dropped along the inner wall of a reaction vessel when the reagent is dispensed by using a dispensing mechanism in which the tip of a nozzle has a substantially circular arc shape when the reagent is dispensed into the sample. However, in this method, the position to dispense the reagent depends on the stopping accuracy of a reagent dispensing mechanism and the dimensional errors of individual detection sections. Due to this, a distance between the nozzle for dispensing the reagent and the inner wall of the reaction vessel is not constant and the conditions for dispensing the reagent into the sample vary each time, and therefore, an air bubble may be entrained. Further, since the conditions for dispensing the reagent into the sample vary each time, a problem may be caused in reproducibility of measurement results. In addition, a structure to stir the sample and the reagent separately is needed. At present, as market needs for an automatic analyzer that analyzes the amount of a component contained in a sample such as blood or urine, an automatic analyzer that has high performance, is space-saving, and is inexpensive has been demanded.

Under such circumstances, an object of the invention is to enable reduction in cost and space-saving by performing mixing of a sample and a reagent by the momentum generated when the reagent is discharged so that a stirring mechanism is no longer needed. Another object of the invention is to provide an automatic analyzer characterized in that the position to dispense the reagent does not depend on the stopping accuracy of a dispensing mechanism and the dimensional errors of individual detection sections, and the stopping at the same position is achieved each time, so that a part for controlling the stopping position such as a sensor is not used, thereby realizing reduction in cost. In addition, an automatic analyzer with high reproducibility of measurement results can be provided.

Solution to Problem

A representative example of the invention of this application is an automatic analyzer which includes a nozzle that sucks and discharges a reagent for a blood clotting reaction, a control section that controls the suction and discharge of the reagent by the nozzle, a nozzle driving mechanism that changes the position of the nozzle, and a clotting time detection section that is mounted with a reaction vessel in which a sample and the reagent are mixed and detects the clotting time of the sample, wherein the nozzle driving mechanism presses the nozzle against the side surface of the inner wall of the reaction vessel with respect to the reaction vessel into which the sample is dispensed, and the control section discharges the reagent into the reaction vessel in a state where the nozzle is pressed against the side surface of the inner wall.

Advantageous Effects of Invention

According to the invention, by pressing the nozzle that dispenses the reagent against the side surface of the inner wall of the reaction vessel, the position to dispense the reagent can be maintained constant. Further, by pressing the nozzle that dispenses the reagent against the side surface of the inner wall of the reaction vessel, the reagent drops along the inner wall of the reaction vessel, and therefore, it becomes possible to dispense the reagent without entraining an air bubble in the mixed liquid of the sample and the reagent. By preventing air bubble entrainment, disturbance which hinders accurate optical measurement can be prevented, and therefore, reduction in accuracy of measuring a blood clotting ability can be prevented. Further, the position to discharge the reagent is hardly affected by the stopping accuracy of the dispensing mechanism or the like, and therefore, an automatic analyzer with high reproducibility of measurement results can be provided. In addition, in the dispensing of the reagent such that the position to dispense the reagent is kept constant and an air bubble is not entrained in the mixed liquid of the sample and the reagent, by stirring the sample and the reagent by the momentum generated when the reagent is discharged, a stirring mechanism is no longer needed, and therefore, an automatic analyzer which can achieve reduction in cost and space-saving can be realized.

DESCRIPTION OF EMBODIMENTS

Hereinafter, embodiments of the invention will be described in detail with reference to the drawings. Incidentally, the drawings show exemplary embodiments of the invention and do not limit the embodiments of the invention. Further, members having the same function are basically denoted by the same reference numerals throughout the drawings for explaining the embodiments and repeated explanation thereof is omitted as much as possible.

Figure 1:
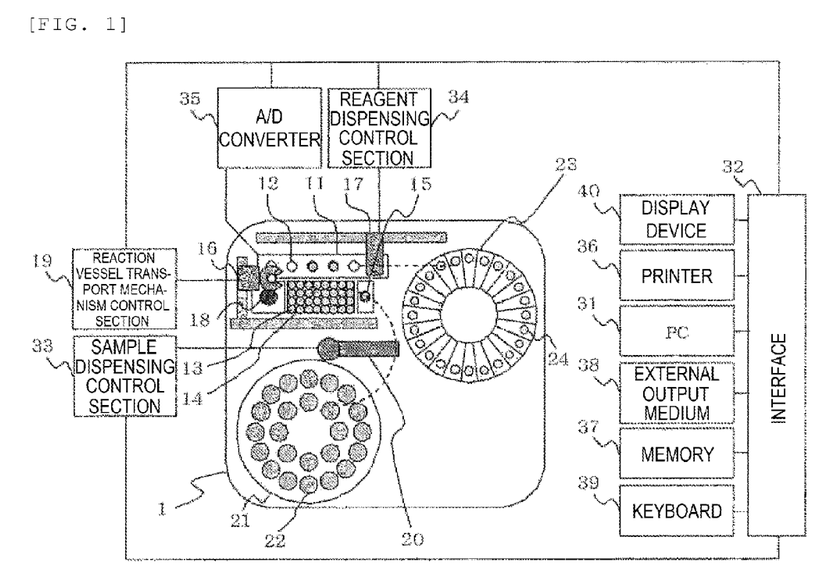
FIG. 1 is a system block diagram showing the overall structure of a blood clotting time measurement device of one example of the invention.

FIG. 1 is a system block diagram showing the overall structure of a blood clotting ability measurement device serving as a base of one example of the invention. As shown in FIG. 1, the blood clotting ability measurement device is constituted by a reaction vessel temperature control block 11 including a plurality of clotting time detection sections 12, a reaction vessel supply section 14 in which a plurality of disposable reaction vessels 13 to be used for measurement are stocked, a reaction vessel transport mechanism 16 that transports the disposable reaction vessel 13, a reagent dispensing mechanism with a reagent heating function 17, a reaction vessel disposal section 18, a sample dispensing mechanism 20, a sample disk 21, and a reagent disk 23, and a computer 31.

Next, an outline of the motion of the mechanism of measurement of a blood clotting time will be described. By the reaction vessel transport mechanism 16, the disposable reaction vessel 13 is transported from the reaction vessel supply section 14 to a clotting time sample dispensing position 15. A sample dispensed into the sample dispensing mechanism 20 is dispensed into the disposable reaction vessel 13 at the clotting time sample dispensing position 15 through a sample dispensing position in a biochemical analysis section. By the reaction vessel transport mechanism 16, the disposable reaction vessel 13 into which the sample is dispensed is transported to the clotting time detection section 12 included in the reaction vessel temperature control block 11, and the sample is heated to 37° C. A reagent for a blood clotting reaction is sucked from a reagent vessel 24 by the reagent dispensing mechanism with a reagent heating function 17 and preheated to 37° C. The reagent after completion of preheating is discharged to the disposable reaction vessel 13 containing the sample. At this time, the sample and the reagent are also stirred by the momentum of the discharged reagent, and the measurement of the blood clotting time is started. The disposable reaction vessel 13 after completion of the measurement of the blood clotting time is disposed of in the reaction vessel disposal section 18 by the reaction vessel transport mechanism 16.

Next, a control system and a signal processing system in an automatic analyzer 1 shown in FIG. 1 will be briefly described. The computer 31 (control section) is connected to a reaction vessel transport mechanism control section 19, a sample dispensing control section 33, a reagent dispensing control section 34, and an A/D converter 35 through an interface 32. The computer 31 sends a command to the reaction vessel transport mechanism control section 19 and controls a reaction vessel transport motion. Further, the computer 31 sends a command to the sample dispensing control section 33 and controls a sample dispensing motion. In addition, the computer 31 sends a command to the reagent dispensing control section 34 and controls a reagent dispensing motion.

A photometric value converted to a digital signal by the A/D converter 35 is incorporated into the computer 31. The computer 31 determines the sample clotting time based on the incorporated measurement value.

To the interface 32, a printer 36 for performing printing, a memory 37 which is a storage device, an external output medium 38, a keyboard 39 for inputting an operation command or the like, and a CRT display (display device) 40 for displaying on a screen are connected. As the display device 40, other than a CRT display, a liquid crystal display or the like can be adopted. The memory 37 is constituted by, for example, a hard disk memory or an external memory. The memory 37 stores the information of the password of each operator, the display level of each screen, analysis parameters, the contents of request of analysis items, calibration results, analysis results, and the like.

Figure 2:
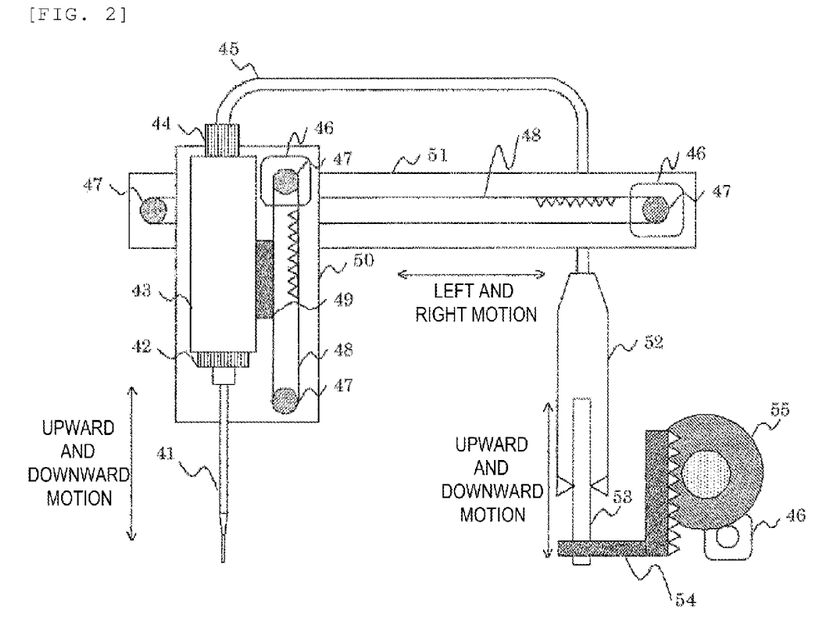
FIG. 2 is an outline view of a reagent dispensing mechanism which is one embodiment of the invention.

FIG. 2 shows an outline view of a liquid holding section, a driving section that changes the position of the liquid holding section, and a mechanism that changes the holding position of a liquid 56 of the reagent dispensing mechanism 17 related to the invention. First, the respective configurations will be described. The liquid holding section is constituted by a nozzle 41 that sucks and discharges a reagent for a blood clotting reaction, a heat block 43 that heats the liquid 56, a nozzle connection section 42 that connects the nozzle 41 to the heat block 43, a flow channel 45 that connects the liquid holding section and the mechanism that changes the holding position of the liquid 56, and a flow channel connection section 44 that connects the flow channel 45 to the heat block 43.

In the nozzle driving mechanism that changes the position of the liquid holding section, a motor 46 is fixed to a vertical base 50, a pulley 47 is fixed to each of the motor 46 and the vertical base 50, a belt 48 connects between the pulleys 47, and the belt 48 and the reagent dispensing mechanism 17 are fixed by a driving mechanism connection section 49. The motor 46 is fixed to a horizontal base 51, a pulley 47 is fixed to each of the motor 46 and the horizontal base 51, a belt 48 connects between the pulleys 47, and the belt 48 of the horizontal base 51 and the vertical base 50 are fixed. The driving method and the fixing method described here are merely examples and do not limit the invention.

The liquid holding section is disposed between the nozzle 41 and the below-mentioned syringe section (driving mechanism). The flow channel connects the liquid holding section and the syringe section (driving mechanism). The heat block 43 performs heating with a heater and the liquid 56 is heated through the heat block. The method of heating the liquid 56 is not limited thereto, and as the heating method, a member similar to the heater may be used. For example, heating of the liquid 56 by an electric heating wire or a Peltier element is considered. Incidentally, the heater represented by an electric heating wire or a Peltier element and the heat block 43 are different members in a strict sense, however, in this description, the heat block 43 including the heater is referred to as "heater". The mechanism that changes the holding position of the liquid 56 is constituted by an outer cylinder 52 and a plunger 53 as the syringe section, a rack 54 and a motor 46 for moving upward and downward the plunger 53, and a gear 55 that transmits the motion of the motor 46 to the rack 54. By changing the pressure in the nozzle 41 by the syringe section (driving mechanism), the reagent is sucked and discharged. The syringe section (driving mechanism) is controlled by the reagent dispensing control section 34 (control section). Accordingly, the suction and discharge of the reagent by the nozzle 41 is controlled by the reagent dispensing control section 34.

Next, the motion will be described. First, as for the upward and downward motion of the reagent dispensing mechanism 17, the rotary motion of the motor 46 fixed to the vertical base 50 is converted to the upward and downward motion through the pulley 47 and the belt 48. Further, as for the left and right motion of the reagent dispensing mechanism 17, the rotary motion of the motor 46 fixed to the horizontal base 51 is converted to the left and right motion through the pulley 47 and the belt 48. As for the motion of the syringe section (driving mechanism), the rotary motion of the motor 46 is transmitted to the rack 54 through the gear 55 and converted to the upward and downward motion. By moving upward and downward the plunger 53 connected to the rack 54, the liquid 56 is sucked from the tip of the nozzle 41, and the liquid 56 is drawn into the heat block 43, and then, the liquid 56 is heated.

The liquid 56 at this time not only indicates a reagent, but also includes a diluted liquid and a sample. That is, the nozzle 41 can also suck and discharge a sample depending on the analysis item, and the nozzle 41 can be used in common for the reagent and the sample.

Figure 3:
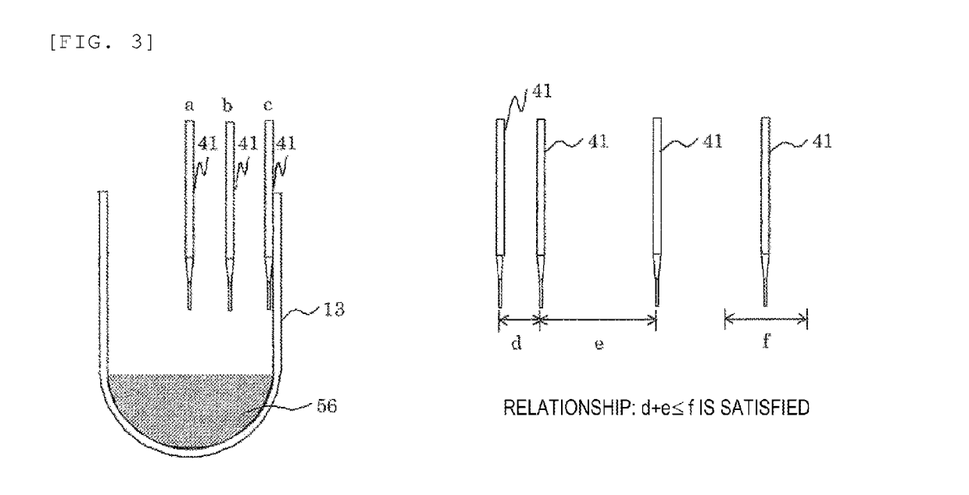
FIG. 3 is an outline view of a liquid holding section which is one embodiment of a related art.

FIG. 3 illustrates an appropriate position of the nozzle 41 for stirring the sample and the reagent by the momentum generated when the reagent is discharged and the conditions in which the nozzle 41 can be stopped at the same position each time by pressing the nozzle 41 against the inner wall of the disposable reaction vessel 13 within the elastic range of the nozzle 41 in the dispensing of the reagent such that the position to dispense the reagent is kept constant and an air bubble is not entrained in the mixed liquid of the sample and the reagent.

First, an appropriate position of the nozzle 41 when the reagent is dispensed will be described. The positions of the nozzle 41 between the central position and the inner wall of the disposable reaction vessel 13 in the order from the central position are represented by a, b, and c. First, in the case where the reagent is dispensed at the position a, the reagent is dispensed as if the reagent beats the liquid surface of the liquid 56, and therefore, an air bubble is easily entrained in the mixed liquid of the liquid 56 and the reagent, and thus, also the two liquids are not well mixed. In the case where the reagent is dispensed at the position b, air bubble entrainment is prevented as compared with the case where the reagent is dispensed at the position a and the two liquids are well mixed, however, air bubble entrainment is not completely eliminated, and therefore, the position b cannot be said to be an appropriate position to dispense the reagent. Subsequently, in the case where the reagent is dispensed at the position c, the reagent is dispensed along the inner wall of the disposable reaction vessel 13, and therefore, air bubble entrainment in the mixed liquid can be prevented. In addition, also the two liquid are mixed well, and therefore, the position c can be said to be an appropriate position to dispense the reagent. Further, also with respect to the accuracy of stopping the nozzle 41, by pressing the nozzle 41 against the side surface of the inner wall of the disposable reaction vessel 13, it becomes possible to stop the nozzle 41 at the same position each time. This is because the nozzle 41 has an elongated shape in the vertical direction, and therefore, the nozzle 41 can be elastically deformed in the horizontal direction, and thus, by pressing the nozzle 41, the variation in accuracy of stopping the nozzle 41 can be absorbed.

Next, a method of motion of the nozzle 41 to the position to discharge the reagent will be described. First, the conditions in which the nozzle 41 can be stopped at the same position each time with respect to the axial direction will be described. Here, a case where the clotting time detection section is composed of a plurality of detection sections capable of being simultaneously mounted with a plurality of reaction vessels, and dimensional errors of individual detection sections occur will be described. The positional error of the nozzle 41 with respect to the disposable reaction vessel 13 caused by the dimensional errors of individual detection sections is represented by d. Then, the positional error due to the stopping accuracy of the reagent dispensing mechanism 17 is represented by e. Finally, in the case where the range of the elastic deformation in the horizontal direction of the nozzle 41 is represented by f, as the conditions in which the nozzle 41 can be stopped at the same position each time, the following relationship is satisfied: $d+e \leq f$. Incidentally, the "range of the elastic deformation in the horizontal direction" as used herein refers to the amount of displacement in the horizontal direction of the tip of the nozzle and the root of the nozzle, in which when the tip of the nozzle is bent in the horizontal direction and then restored to its original state, the nozzle can be returned to its original shape without deforming the nozzle.

Figure 4:
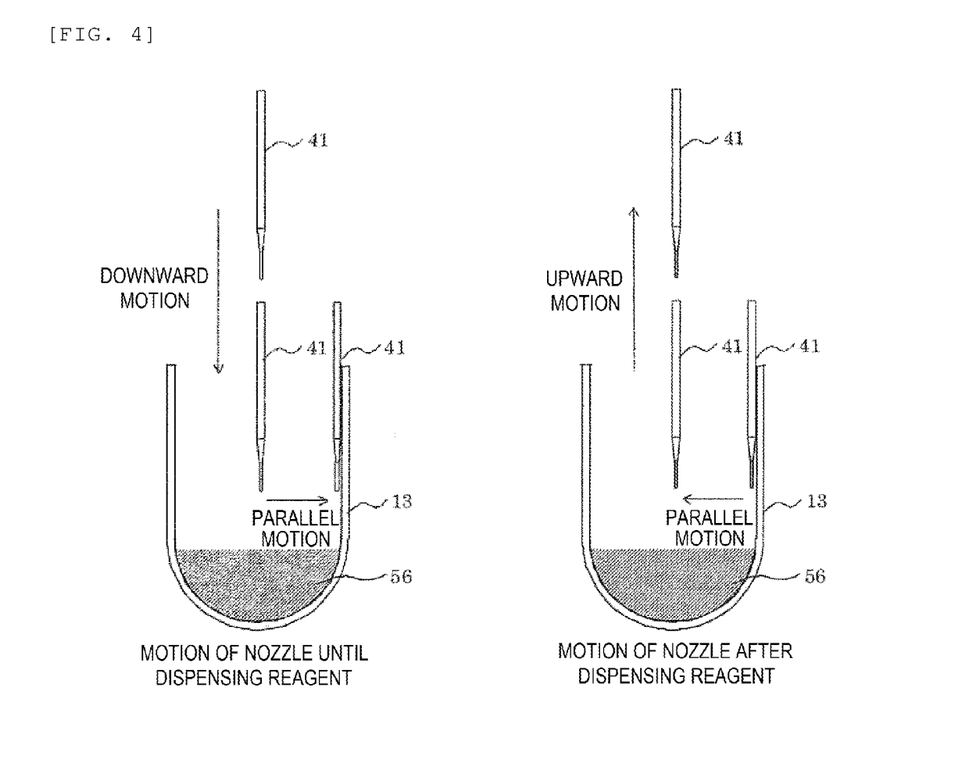
FIG. 4 is an outline view of a liquid holding section which is one embodiment of the invention.

FIG. 4 illustrates a method of motion of the nozzle 41 to the position to discharge the reagent and a method of motion of the nozzle 41 after dispensing the reagent. First, with respect to the method of motion of the nozzle 41 to the position to discharge the reagent, when the nozzle 41 comes to the central position of the disposable reaction vessel 13, the nozzle 41 moves downward to the height at which the nozzle 41 discharges the reagent. Subsequently, the nozzle 41 moves in parallel until the nozzle 41 is pressed against the side surface of the inner wall of the disposable reaction vessel 13, and the nozzle discharges the reagent in a state of being pressed against the side surface. By the momentum of this discharged reagent, the reagent and the sample having been dispensed in advance are stirred. Therefore, it is not necessary to perform stirring using a stirring mechanism. By performing the downward motion at the central position of the disposable reaction vessel 13 in advance, the tip of the nozzle 41 is prevented from coming in contact with the disposable reaction vessel 13. Incidentally, as for the amount of the parallel motion at this time, by adding at least errors d+e to the radius of the disposable reaction vessel 13, even if there are dimensional errors of individual detection sections or there is a positional error of the nozzle 41, the nozzle 41 can be brought into contact with the side surface of the inner wall of the disposable reaction vessel 13. Further, as described above, d+e is not more than f. In this manner, the nozzle driving mechanism can discharge the reagent at the same reagent discharge position each time by driving the nozzle in a given amount capable of ignoring the above errors within the range of the elastic deformation in the horizontal direction of the nozzle and toward the side surface of the inner wall.

Next, the method of motion after discharging the reagent will be described. After dispensing the reagent, the nozzle moves in parallel and thereafter moves upward. By not moving upward first, but moving in parallel first, vibration of the tip of the nozzle 41 by the elastic force stored in the nozzle 41 is prevented, and therefore, the scattering of the reagent from the tip of the nozzle 41 is prevented.

Figure 5:
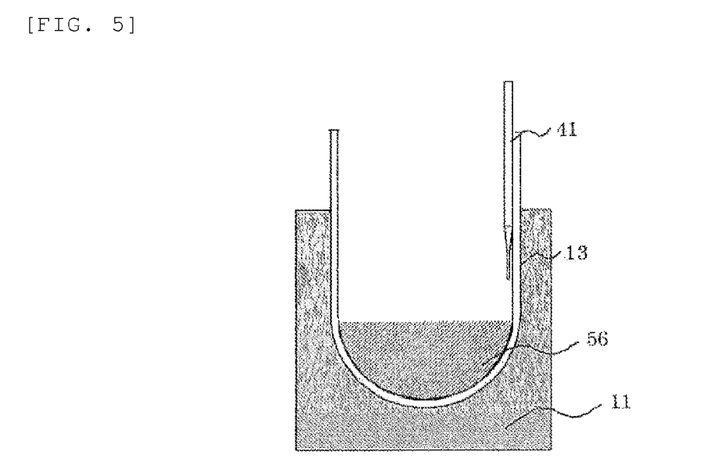
FIG. 5 is a schematic view showing the temperature gradient of a heat block which is one embodiment of the invention.

FIG. 5 shows a method of preventing the decrease in the liquid temperature when the liquid is dispensed into the disposable reaction vessel 13. The nozzle 41 is disposed away from the heat block 43, and therefore, it is difficult to sufficiently heat the nozzle 41. Due to this, it is presumed that the liquid temperature decreases when the liquid passes through the nozzle 41. When the liquid temperature decreases, it is difficult to reproduce the reaction carried out in the body, and therefore, a desired measurement result may not be obtained. In light of this, in order to sufficiently heat the nozzle 41, it is considered that the entire surface is covered with a heat insulating material or the nozzle 41 is brought as close as possible to the heat block 43 by shortening the nozzle 41. However, in consideration of the dispensing of the sample or the reagent, washing, or the like, it is essential that the length of the tip of the nozzle 41 in a state of being not covered be ensured, and therefore, it is not a practical solution. As a method of solving such a problem, it is considered that the nozzle 41 is brought into contact with the disposable reaction vessel 13 whose temperature is controlled in the reaction vessel temperature control block 11. In order to heat the reagent to a desired temperature, the reagent is held in the heat block 43 for a while. By bringing the nozzle 41 into contact with the disposable reaction vessel 13 whose temperature is controlled for this holding time, the temperature can be controlled without spending extra time. In this manner, the clotting time detection section includes the reaction vessel temperature control block 11 as a heating source capable of controlling the temperature, and also the nozzle 41 is pressed against the side surface of the inner wall of the disposable reaction vessel, whereby the decrease in the liquid temperature can be suppressed.

Figure 6:
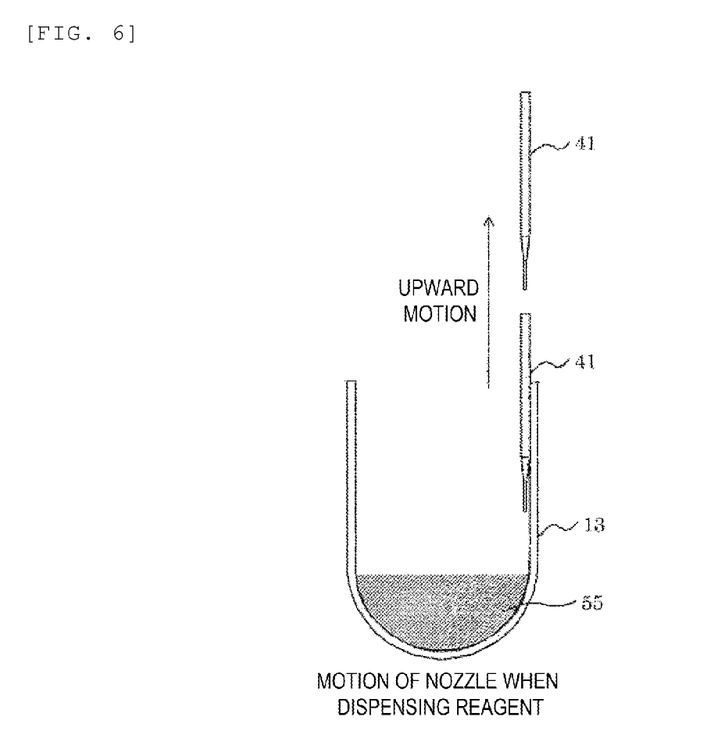
FIG. 6 is a view showing a dispensing method which is one embodiment of the invention.

FIG. 6 shows a dispensing method for preventing the liquid from entering a small gap between the nozzle 41 and the disposable reaction vessel 13 when the liquid is dispensed. It is presumed that even if the nozzle 41 is brought into close contact with the disposable reaction vessel 13, a small gap may be formed. Due to this, when the liquid is dispensed, the liquid enters the gap by a capillary phenomenon, and therefore, accurate dispensing may be hindered. Due to this, by moving the nozzle 41 upward while dispensing the liquid, the liquid is prevented from entering a small gap between the nozzle 41 and the disposable reaction vessel 13. In this manner, by discharging the reagent while moving the nozzle upward in a state of being pressed against the side surface of the inner wall of the disposable reaction vessel, the entering of the liquid can be prevented, and thus, accurate dispensing can be realized.

Figure 7:
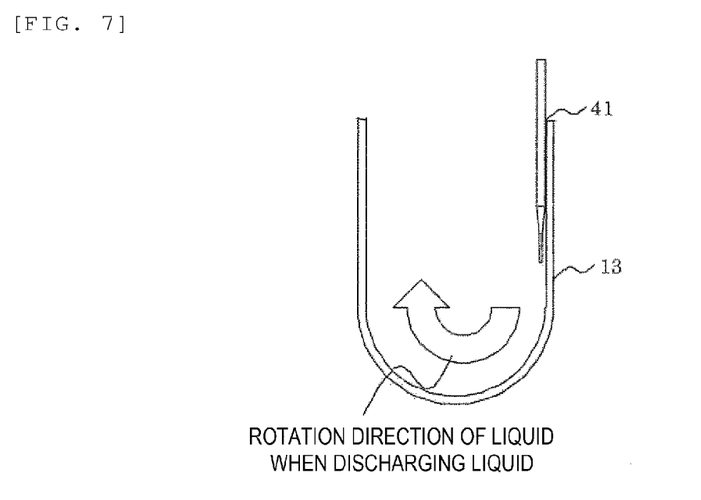
FIG. 7 is a view showing a dispensing method which is one embodiment of the invention.
Figure 8:
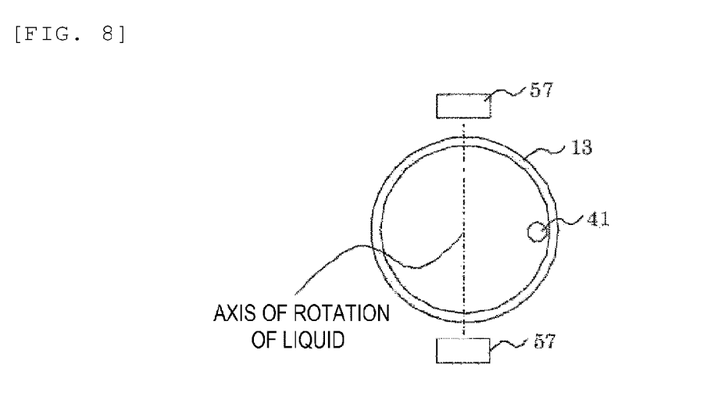
FIG. 8 is an upper view with respect to the dispensing method shown in FIG. 7.

FIG. 8 is an upper view of FIG. 7 and shows a most suitable direction of pressing the nozzle when using a plurality of detectors 57. As one example, a case where two detectors 57 are used is shown. It is considered that a plurality of detectors 57 are used for reducing the effect of noise when measuring the clotting time. In this case, the clotting time detection section includes a light source that irradiates light from the bottom surface of the disposable reaction vessel 13 and two detectors disposed on the side surface of the disposable reaction vessel 13 and facing each other. These two detectors detect light scattered by the sample, and from this detection result, the clotting time is calculated.

At this time, it is necessary to consider the direction of pressing the nozzle in relation to the placement of the detectors 57. The reason therefor is that as shown in FIG. 7, when the liquid is discharged, there is a rotation direction of the liquid. Due to this, when the detectors 57 are disposed at a position away from the axis of this rotation direction, the detectors perform detection in two directions in which the stirring state of the liquid is different, and therefore, it is difficult to determine whether the difference in data detected by the two detectors 57 is due to a difference in the stirring state or due to the effect of noise. Therefore, as shown in FIG. 8, it is desired to control the direction of pressing the nozzle so that the detectors 57 are disposed on the axis of rotation of the liquid. That is, the nozzle driving mechanism desirably drives the nozzle in the vertical direction with respect to a straight line connecting the two detectors after moving the nozzle downward to a predetermined depth of the reaction vessel, and discharges the reagent while pressing the nozzle against the reaction vessel. Incidentally, the "vertical direction" as used herein does not necessarily mean "vertical" in a strict sense, and may be substantially vertical including a certain amount of error.

Figure 9:
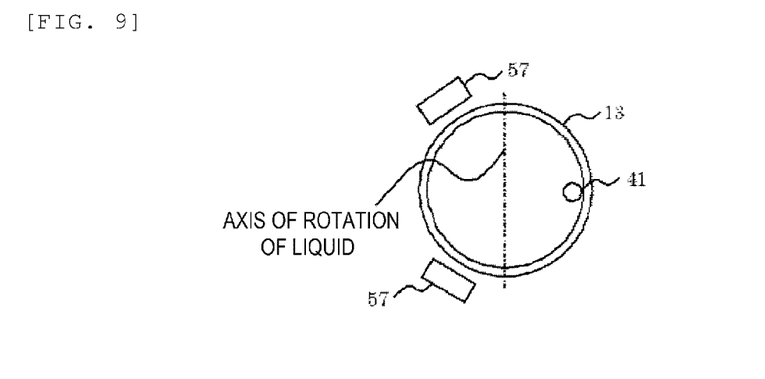
FIG. 9 is a view showing another example of the placement of the detectors shown in FIG. 8.
Figure 10:
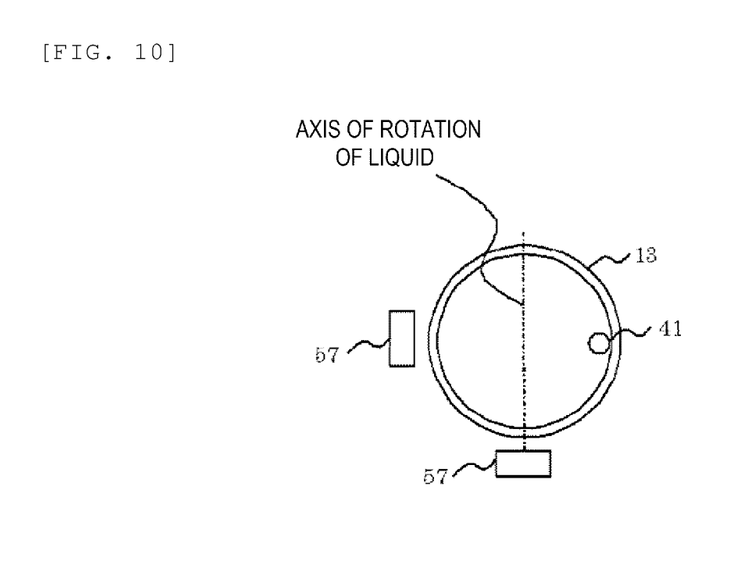
FIG. 10 is a view showing still another example of the placement of the detectors shown in FIG. 8.

The placement of the detectors 57 may be bilaterally symmetric with respect to the axis of rotation of the liquid, and therefore, the placements shown in FIGS. 9 and 10 are also possible. In the case where a plurality of detectors 57 are disposed, here, a case where two detectors are used is shown as an example, a case where the detectors face each other as shown in FIG. 8 and a case where the detectors are disposed at a certain angle as shown in FIGS. 9 and 10 are considered. Among these, a desired placement of the detectors 57 is the placement in which the detectors face each other shown in FIG. 8. In a blood clotting test, as described above, a reaction process is measured from the beginning to the end of the test, and therefore, the blood clotting detection section 12 is occupied by one detection until the completion of the reaction. Due to this, it is necessary to connect a plurality of detection sections in consideration of processing ability, cost, and temperature controllability. At this time, by disposing the detectors 57 facing each other, a structure of the detection sections is more simplified than any other placements, and also the production can be achieved at low cost. In addition, when considering the reduction in cost, a case where one detector 57 is provided is considered. In this case, the detector 57 may be disposed at any place. However, in the case where a plurality of detection sections are provided, the detector 57 is desirably disposed in the same direction in order to see the correlation between the detection sections.

Incidentally, it has also been described that the sample can be discharged by the nozzle 41, however, when the sample is discharged into the disposable reaction vessel 13, the sample may be discharged in a state where the nozzle is pressed against the side surface of the inner wall of the reaction vessel in the same manner as the reagent, or the sample may be dispensed by bringing the nozzle into contact with the bottom surface of the inner wall of the disposable reaction vessel 13. It goes without saying that the method is not limited to these methods of dispensing the sample, and the reagent is discharged above the liquid surface of the dispensed sample.

By adopting the configuration as in this Example, the position to dispense the reagent can be kept constant by pressing the nozzle having elasticity in a vertical direction with respect to the axial direction in which the reagent is dispensed against the side surface of the inner wall of the reaction vessel within the elastic range of the nozzle. In addition, by pressing the nozzle that dispenses the reagent against the inner wall of the reaction vessel, the reagent drops along the side surface of the inner wall of the reaction vessel, and therefore, it becomes possible to dispense the reagent without entraining an air bubble in the mixed liquid of the sample and the reagent. By preventing air bubble entrainment, disturbance which hinders accurate optical measurement can be prevented, and therefore, reduction in accuracy of measuring a blood clotting ability can be prevented. Further, in the dispensing of the reagent such that the position to dispense the reagent is kept constant and an air bubble is not entrained in the mixed liquid of the sample and the reagent, by stirring the sample and the reagent by the momentum generated when the reagent is discharged, a stirring mechanism is no longer needed, and therefore, an automatic analyzer which can achieve reduction in cost and space-saving can be realized. In addition, an automatic analyzer with high reproducibility of measurement results can be provided.

REFERENCE SIGNS LIST 1 blood clotting ability measurement device
11 reaction vessel temperature control block
12 clotting time detection section
13 disposable reaction vessel
14 reaction vessel supply section
15 clotting time sample dispensing position
16 reaction vessel transport mechanism
17 reagent dispensing mechanism with a reagent heating function
18 reaction vessel disposal section
19 reaction vessel transport mechanism control section
20 sample dispensing mechanism
21 sample disk
22 sample vessel
23 reagent disk
24 reagent vessel
31 computer
32 interface
33 sample dispensing control section
34 reagent dispensing control section
35 A/D converter
36 printer
37 memory
38 external output medium 39 keyboard
40 CRT display (display device)
41 nozzle
42 nozzle connection section
43 heat block
44 flow channel connection section
45 flow channel
46 motor
47 pulley
48 belt
49 driving mechanism connection section
50 vertical base
51 horizontal base
52 outer cylinder
53 plunger
54 rack
55 gear
56 liquid
57 detector

The invention claimed is:

1. An automatic analyzer, comprising:
a reaction vessel;
a nozzle that sucks and discharges a reagent for a blood clotting reaction into the reaction vessel;
a nozzle driving mechanism that moves the nozzle;
a control section that controls the suction and discharge of the reagent by the nozzle and controls the motion of the nozzle driving mechanism; and
a clotting time detection section that includes a light source configured to irradiate light from a bottom surface of the reaction vessel in which a sample and the reagent are mixed and two detectors disposed along a side surface of the reaction vessel facing each other and configured to detect light scattered from the sample in the reaction vessel corresponding to the blood clotting reaction of the sample,
wherein the control section is configured to:
move the nozzle in a downward direction to a predetermined depth into the reaction vessel, thereafter move the nozzle in a lateral direction which is substantially perpendicular to a line connecting the two detectors into contact with an inner wall of the reaction vessel, and thereafter press the nozzle towards a side surface of the inner wall within a predetermined range of elastic deformation of the nozzle satisfying "d+e≤f", and
discharge the reagent into the reaction vessel in a state where the nozzle is pressed against the side surface of the inner wall,
wherein a predetermined positional error of the nozzle with respect to the reaction vessel is represented by "d", a predetermined positional error of a stopping position of the nozzle driving mechanism is represented by "e", and the predetermined range of elastic deformation in a lateral direction of the nozzle is represented by "f".

2. The automatic analyzer according to claim 1, wherein the discharge of the reagent into the reaction vessel stirs the reagent and the sample in the reaction vessel.

3. The automatic analyzer according to claim 1, wherein the clotting time detection section is a detection section including a temperature-controllable heat source.

4. The automatic analyzer according to claim 1, wherein the control section is configured to suck and discharge the sample into the reaction vessel using the nozzle.

5. The automatic analyzer according to claim 4, wherein the control section is configured to:
discharge the sample while the nozzle is pressed against the side surface of the inner wall of the reaction vessel, and discharge the reagent into the reaction vessel from above a liquid surface of the discharged sample and while the nozzle is pressed against the side surface of the inner wall.

6. The automatic analyzer according to claim 4, wherein the control section is configured to:
discharge the sample while moving the nozzle into contact with a bottom surface of the inner wall of the reaction vessel, and discharge the reagent into the reaction vessel from above a liquid surface of the dispensed sample and while the nozzle is pressed against the side surface of the inner wall.

7. The automatic analyzer according to claim 1, wherein the clotting time detection section includes a plurality of detection sections capable of being simultaneously mounted with a plurality of reaction vessels.

8. The automatic analyzer according to claim 1, wherein the clotting time detection section includes a plurality of detection sections capable of being simultaneously mounted with a plurality of reaction vessels, and
wherein the positional error "d" of the nozzle corresponds to dimensional errors of the individual detection sections.

9. The automatic analyzer according to claim 1,
wherein the lateral direction is substantially perpendicular to a light receiving axis at which the detectors receive the light from the light source.

10. An automatic analyzer according, comprising:
a reaction vessel;
a nozzle that sucks and discharges a reagent for a blood clotting reaction into the reaction vessel;
a nozzle driving mechanism that moves the nozzle;
a control section that controls the suction and discharge of the reagent by the nozzle and controls the motion of the nozzle driving mechanism; and
a clotting time detection section that includes a light source configured to irradiate light from a bottom surface of the reaction vessel in which a sample and the reagent are mixed and a detector disposed along a side surface of the reaction vessel and configured to detect light scattered from the sample in the reaction vessel corresponding to the blood clotting reaction of the sample, and
wherein the control section is configured to:
move the nozzle in a downward direction to a predetermined depth into the reaction vessel, thereafter move the nozzle in a lateral direction which is substantially perpendicular to an optical axis of the detector into contact with an inner wall of the reaction vessel, and thereafter press the nozzle towards a side surface of the inner wall within a predetermined range of elastic deformation of the nozzle satisfying "d+e≤f", and
discharge the reagent into the reaction vessel in a state where the nozzle is pressed against the side surface of the inner wall,
wherein a predetermined positional error of the nozzle with respect to the reaction vessel is represented by "d", a predetermined positional error of a stopping position of the nozzle driving mechanism is represented by "e", and the predetermined range of elastic deformation in a lateral direction of the nozzle is represented by "f".

11. An automatic analyzer, comprising:
a reaction vessel;
a nozzle that sucks and discharges a reagent for a blood clotting reaction into the reaction vessel;
a nozzle driving mechanism that moves the nozzle;

a control section that controls the suction and discharge of the reagent by the nozzle and controls the motion of the nozzle driving mechanism; and a clotting time detection section that is mounted with the reaction vessel in which a sample and the reagent are mixed and detects the clotting time of the sample, wherein the clotting time detection section includes a light source that configured to irradiate light from a bottom surface of the reaction vessel and two detectors disposed along a side surface of the reaction vessel, and wherein the control section is configured to:

move the nozzle in a downward direction to a predetermined depth into the reaction vessel, thereafter move the nozzle in a lateral direction which is substantially perpendicular to an optical axis of one of the detectors into contact with an inner wall of the reaction vessel, and is after press the nozzle towards a side surface of the inner wall within a predetermined range of elastic deformation of the nozzle satisfying "$d+e \leq f$", and discharge the reagent into the reaction vessel in a state where the nozzle is pressed against the side surface of the inner wall, wherein a predetermined positional error of the nozzle with respect to the reaction vessel is represented by "d", a predetermined positional error of a stopping position of the nozzle driving mechanism is represented by "e", and the predetermined range of elastic deformation in a lateral direction of the nozzle is represented by "f".

* * * * *